United States Patent [19]

Austin, Jr. et al.

[11] Patent Number: 5,738,520
[45] Date of Patent: Apr. 14, 1998

[54] THREE-WAY PNEUMATIC VALVE SYSTEM

[75] Inventors: George K. Austin, Jr.; Paul D. Sturges, both of Newberg, Oreg.

[73] Assignee: A-Dec, Inc., Newberg, Oreg.

[21] Appl. No.: 426,613

[22] Filed: Apr. 21, 1995

[51] Int. Cl.[6] .................................................. A61G 15/00
[52] U.S. Cl. ........................... 433/98; 433/77; 254/423;
 280/43.24; 137/625.23
[58] Field of Search ...................... 433/77, 98–101;
 188/5, 7, 19; 254/45, 418, 423; 280/43.24;
 251/310; 137/625.23, 625.24, 625.11, 625.15,
 625.16, 625.21

[56] References Cited

U.S. PATENT DOCUMENTS

| | | | |
|---|---|---|---|
| Re. 28,649 | 12/1975 | Austin, Jr. . | |
| 707,581 | 8/1902 | Gregory | 137/625.21 |
| 735,162 | 8/1903 | Settino | 137/625.23 |
| 799,134 | 9/1905 | Baldick | 137/625.23 |
| 885,145 | 4/1908 | Davis | 137/625.23 |
| 1,630,781 | 5/1927 | Burman | 137/625.23 |
| 1,677,499 | 7/1928 | Smith | 137/625.23 |
| 1,699,387 | 1/1929 | Anderson | 137/625.24 |
| 1,769,534 | 7/1930 | Nattrass | 254/423 |
| 2,327,419 | 8/1943 | Grandy | 137/625.11 |
| 2,538,205 | 1/1951 | Leathermon | 137/625.23 |
| 2,827,924 | 3/1958 | Towler et al. | 137/625.46 |
| 2,878,786 | 3/1959 | Vuillemin | 137/625.23 |
| 3,036,599 | 5/1962 | Doerfler | 137/625.24 |
| 3,106,021 | 10/1963 | Borden . | |
| 3,513,876 | 5/1970 | Tarbox . | |
| 3,610,283 | 10/1971 | Hill | 137/625.23 |
| 3,638,310 | 2/1972 | Austin, Jr. . | |
| 3,672,059 | 6/1972 | Booth . | |
| 3,713,462 | 1/1973 | Bushee | 137/625.21 |
| 3,756,284 | 9/1973 | Breunich . | |
| 3,837,360 | 9/1974 | Bubula | 137/625.46 |
| 3,918,161 | 11/1975 | Morgan et al. | 433/98 |
| 4,118,866 | 10/1978 | Ross et al. . | |
| 4,145,813 | 3/1979 | Hall . | |
| 4,151,647 | 5/1979 | Saupe et al. . | |
| 4,173,827 | 11/1979 | Austin, Jr. . | |
| 4,177,834 | 12/1979 | Bonney | 137/625.23 |
| 4,188,976 | 2/1980 | Austin, Jr. . | |
| 4,230,143 | 10/1980 | Dettmann et al. . | |
| 4,526,197 | 7/1985 | Martin et al. . | |
| 4,632,148 | 12/1986 | Stark, Sr. et al. | 137/625.21 |
| 4,676,750 | 6/1987 | Mason . | |
| 4,767,327 | 8/1988 | Smithwick et al. . | |
| 5,013,240 | 5/1991 | Bailey et al. | 433/77 |
| 5,431,254 | 7/1995 | Kramer et al. | 188/19 |

FOREIGN PATENT DOCUMENTS

| | | | |
|---|---|---|---|
| 613474 | 12/1960 | Italy | 433/99 |
| 2 178 139A | 2/1987 | United Kingdom . | |

*Primary Examiner*—Ralph Lewis
*Attorney, Agent, or Firm*—Klarquist Sparkman Campbell Leigh & Whinston, LLP

[57] ABSTRACT

The system is adapted for use with a portable dental delivery system and provides a selector for activating one of two handpieces. When one of the handpieces is to be activated, the supporting base is lifted from its wheels by a pneumatic support assembly that is controlled by the same valve system.

13 Claims, 3 Drawing Sheets

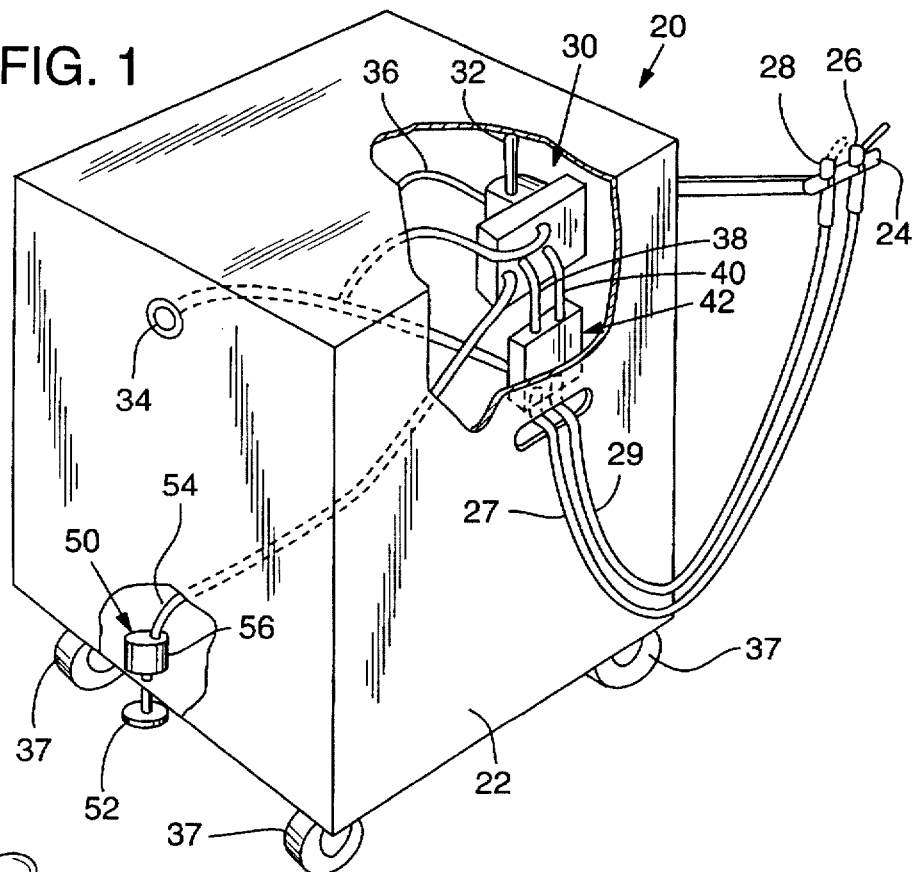
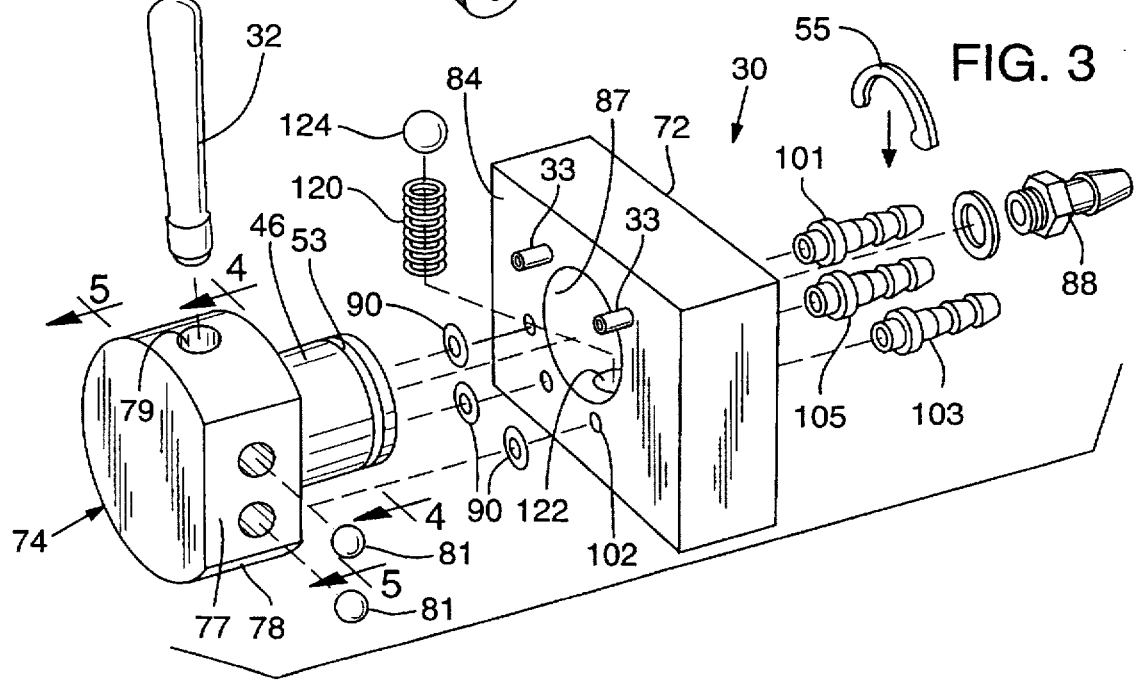

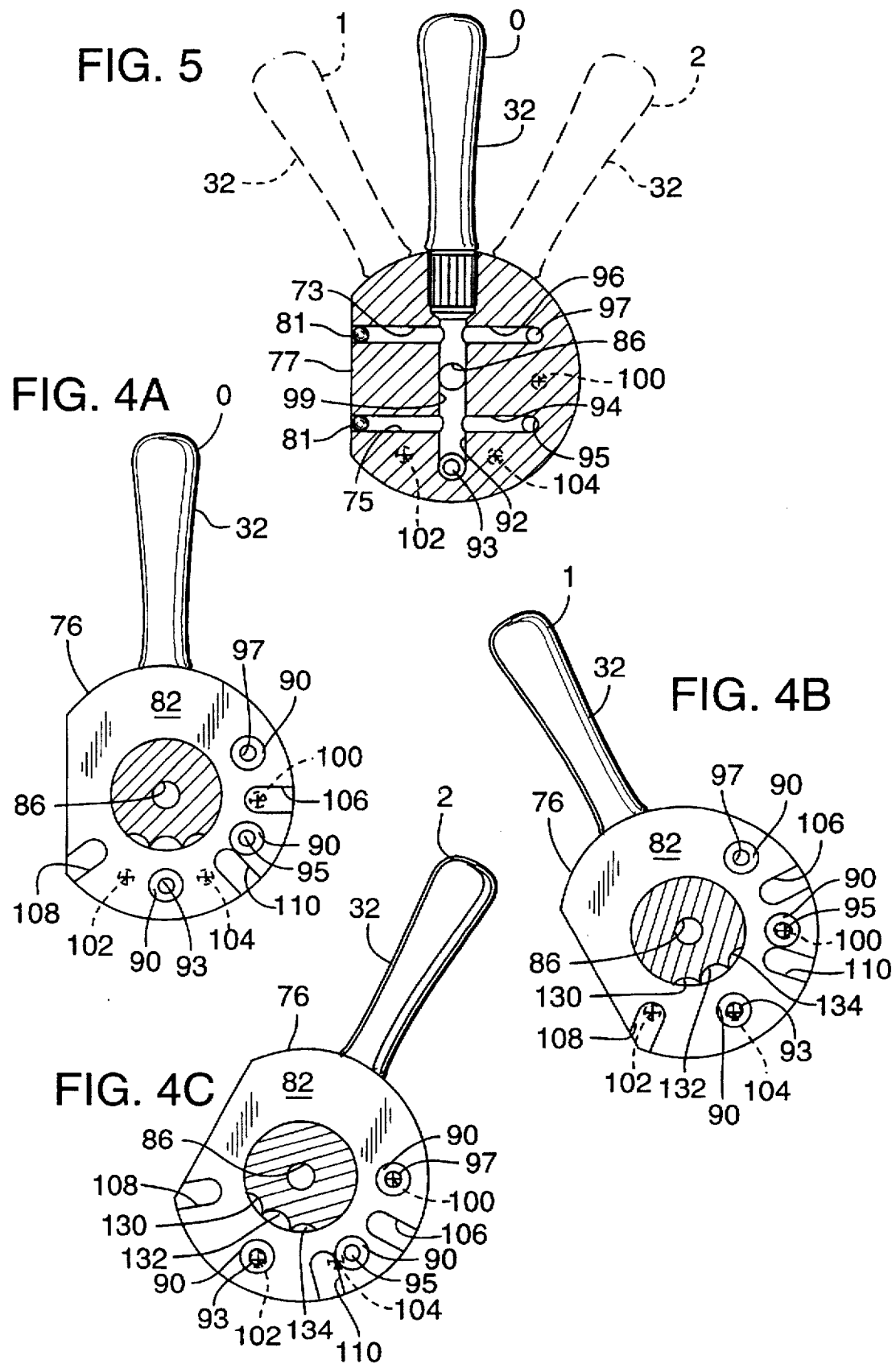

THREE-WAY PNEUMATIC VALVE SYSTEM

TECHNICAL FIELD

This invention relates to a three-way pneumatic valve system that is employed for selectively pressurizing and exhausting three pneumatic conduits of a dental system.

BACKGROUND INFORMATION AND SUMMARY OF THE INVENTION

Modern dental instruments and accessories are often driven or otherwise controlled by pressurized air. The pneumatic control and distribution systems may have any of a multitude of configurations. Manually operated pneumatic valve systems should be uncomplicated, simple to manufacture and assemble, and reliable.

Some pneumatically operated dental equipment comprising dental instruments and their associated drive systems (often collectively referred to as dental delivery systems) may be mounted to portable devices. For example, two or more pneumatically driven dental handpieces may be carried on an instrument holder that is mounted to a wheeled base or cabinet. The base could have mounted to it a manually operable valve system for controlling the operation of the handpieces. The pressurized air employed for driving the handpieces may also be employed for other purposes in conjunction with the portable delivery system.

This invention is directed to a pneumatic valve system for controlling the operation of pneumatically driven dental handpieces. The system is particularly adapted for use with a portable delivery system, and includes a reliable, easy to manufacture and assemble manually operated valve. The system is also adapted for selectively delivering pressurized air to a support assembly that is capable of slightly lifting a wheeled base that carries the delivery system, thereby stabilizing the base for use in its selected location.

BRIEF DESCRIPTION OF THE DRAWINGS

FIG. 1 is a pictorial view of a portable dental delivery system employing the manually operated pneumatic valve system of the present invention.

FIG. 3 is an exploded view showing the primary components of the valve system of the present invention.

FIGS. 4A, 4B and 4C are section views taken along line 4—4 of FIG. 3 showing the selector component of the system in three different positions.

FIG. 5 is a section view taken along line 5—5 of FIG. 3.

DESCRIPTION OF PREFERRED EMBODIMENTS

Figure 2:
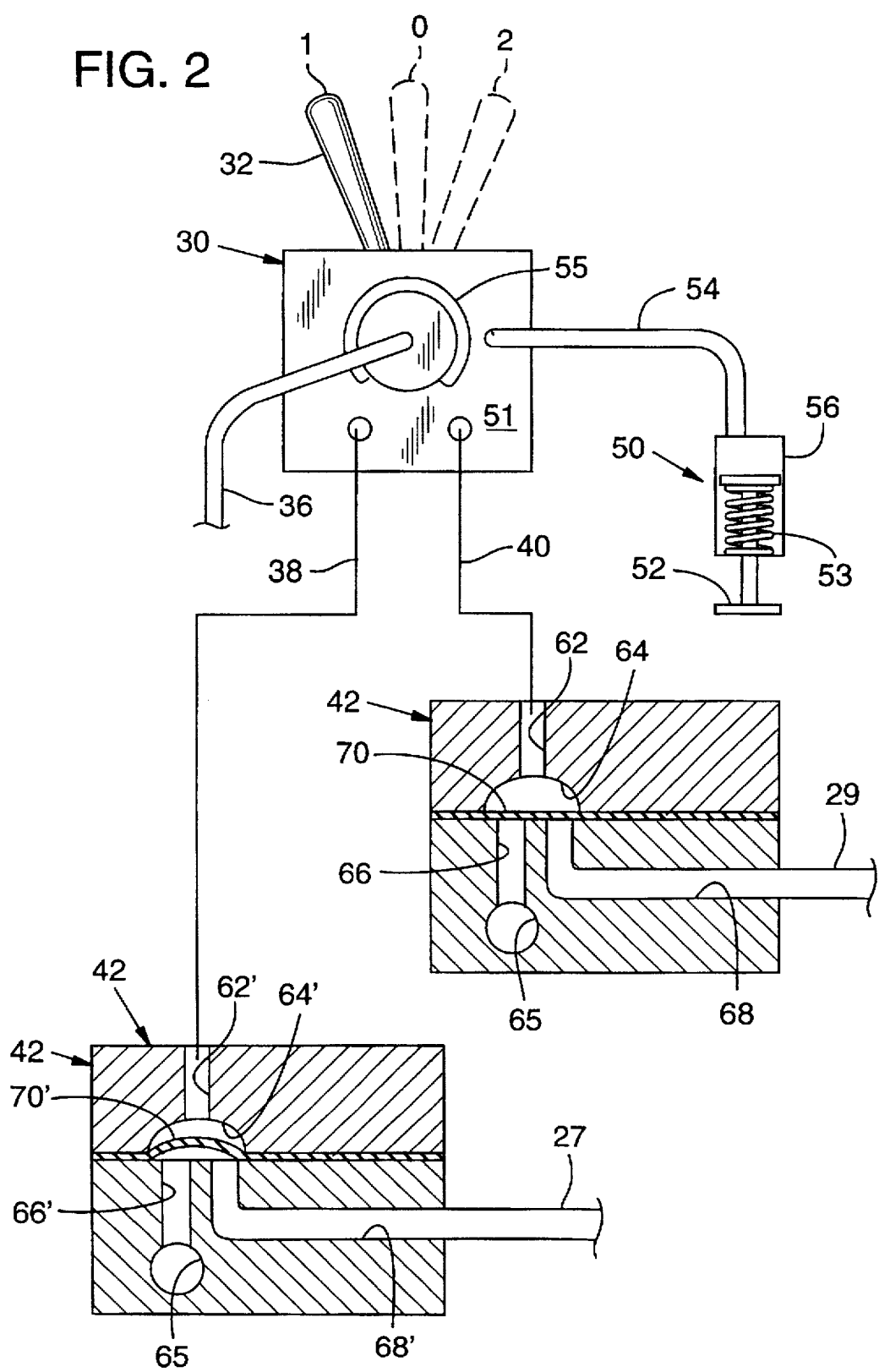
FIG. 2 is a diagram of the valve system of the present invention.

Referring to FIG. 1, the pneumatic valve system of the present invention may be incorporated for use with a portable dental delivery system shown generally as 20 in FIG. 1. The portable delivery system may include a cabinet or base 22 that permits the storage and support of dental equipment. For the sake of simplicity, the base 22 is depicted as solely supporting a instrument-holding arm 24 on which are hung two handpieces that, for convenience, will be referred to as a first handpiece 26 and a second handpiece 28.

Within the base 22 there is mounted a valve assembly 30 from which protrudes a selector handle 32 that may be moved by the user as explained more fully below. An air supply line 34 is carried in the cabinet and is connectable to a source of pressurized air (not shown). The pressurized air supply line 34 is connected to the valve assembly 30 via control line 36 that branches from line 34.

The selector handle 32 may be moved from an "off" or neutral position into either of two other positions for selectively directing the pressurized air received via control line 36 to a first handpiece control line 38 or a second handpiece control line 40. Both of these handpiece control lines 38, 40 are connected to a handpiece control block 42 that is also carried on the base 22 and, although depicted as a separate component, may be constructed to be an integral part of the valve assembly 30.

As will be described below, the handpiece control block 42 is operable to direct to the first handpiece 26 pressurized drive air provided in supply line 34 through a first handpiece drive line 27 that extends between the block 42 and the first handpiece 26. Alternatively, the source of drive air in line 34 may be directed by the handpiece control block 42 through a second handpiece drive line 29, which extends between the block 42 and the second handpiece 28.

Also shown in FIG. 1 is one of four air-driven support assemblies 50 that essentially comprises a cylinder 56 with an extendable and retractable piston 52. One of the assemblies 50 is mounted to the base 22 near each of the four wheels 37 of the base 22. Whenever the base 22 is wheeled into the position selected by the user, pressurized air can be delivered through an associated control line 54 from the valve assembly 30. Whenever the line 54 is thus pressurized, the pistons or feet 52 will extend from the base by an amount sufficient to lift the wheels of the base slightly off the floor, thereby stabilizing the base during use.

Turning now to the schematic diagram of FIG. 2, depicted there is the selector handle 32 movable from the neutral position "0" into a position "1" (solid line) whereby the pressurized air received in the valve assembly via line 36 is directed into the line 54 for pressurizing the cylinder 56 with which the above-described piston 52 is coupled. The pressure in line 54 causes the piston to extend by an amount sufficient to lift the base wheels 37 off the floor. It will be appreciated that line 54 branches into four parts, one part directed to each of the four assemblies 50 that are mounted to the base 22 adjacent to each wheel 37.

When the selector handle 32 is in position "1", the valve assembly 30 also directs the pressurized air to second handpiece control line 40. That line 40 is connected to the handpiece control block 42, and particularly to an inlet passage 62 that opens within the block to a chamber 64.

The drive air supplied via line 34 enters the control block 42 via a passage 65 that includes a branch 66 that terminates at the above-mentioned chamber 64. An outlet passage 68 extends between the chamber 64 to the exterior of the control block 42 where it is coupled to the second handpiece drive line 29.

A deformable diaphragm 70 is secured within the control block 42 to extend across the chamber 64. Whenever the control line 40 is pressurized (as occurs when the handle is in position "1"), hence applying pressure to the diaphragm 70 in chamber 64, the diaphragm moves against and covers the ends of the branch 66 and outlet passage 68 to prevent the drive air from reaching the passage. Accordingly, no drive air reaches the second handpiece. That handpiece is inactive.

The control line 38 of the first handpiece 26 is also connected to the control block 42, which block includes components substantially similar to those just described with respect to the second handpiece. Specifically, the control line 38 connects with a passage 62' that opens to an internal chamber 64'. The drive air supply in passage 65 is directed to the chamber via branch 66'. The drive air passing through the chamber 64' exits via outlet passage 68', which is connected to the drive line 27 that directs the drive air to the first handpiece 26.

With the selector handle 32 in position "1", air in control line 38 is exhausted to atmosphere as will be described. When the air in conduit 38 is exhausted, the pressure in passageway 62' is removed, and the pressure of drive air in branch 66' deforms the diaphragm 70', thereby permitting drive air to flow through the chamber 64' and outlet passage 68' to the first handpiece via drive line 27. Hence, the first handpiece 26 is driven or activated.

When the user wishes to operate the second handpiece 28, and deactivate the first handpiece 26, the selector handle 32 is moved into a position "2" (FIG. 2) whereby the pressurized air received in the valve assembly 30 via line 36 is directed to the first handpiece control line 38. As a result, the pressure developed in connected passageway 62' forces the diaphragm 70' to cover the ends of the branch 66' and outlet passage 68' thereby preventing drive air from reaching the first handpiece drive line 27.

While the selector handle 32 is in position "2", the air in control line 40 is exhausted to atmosphere. When the air in control line 40 is exhausted, the pressure in passageway 62 is removed, and the pressurized air in branch 66 deforms the diaphragm 70 thereby permitting drive air to flow through the chamber 64 and outlet passage 68 to the second handpiece via drive line 29.

Irrespective of whether the selector handle 32 is in position "1" or position "2", pressurized air is directed from the valve assembly 30 to the support assembly line 54. Accordingly, the base is supported on the extended pistons 52 whenever one of the handpieces is used; when the selector handle 32 is in position "1" or position "2".

When the selector handle is moved into the neutral position "0", the pistons 52 are retracted so that the base 22 is again supported on its wheels 37. To this end, the valve assembly 30 is constructed so that when the selector handle is moved to position "0" any air in line 54 is exhausted to atmosphere. As shown in FIG. 2, the pistons are retracted by a spring 53 held within the cylinder 56, which spring is otherwise compressed when line 54 is pressurized and the pistons extended.

With the selector handle 32 in position "0" air in both control line 38 and control line 40 is neither intentionally exhausted to atmosphere nor pressurized. The "0" position is intended for selection when the base 22 is to be moved, without, therefore, using a handpiece while the base remains supported on its wheels. It is noteworthy here that the drive air supply reaching the control block 42 is primarily controlled by a foot-actuated switch (not shown). Accordingly, even though a control line 38 or 40 may be exhausted while the selector is in position "0", drive air should not be delivered to the passageway 65 in the control block (because, for example, the foot switch is made unavailable or otherwise inactivated).

Turning to FIGS. 3–5, the valve assembly 30 generally comprises a valve body 72 and a rotatable selector 74 to which the handle 32 is attached. The selector generally comprises two contiguous cylindrically shaped parts 76, 78. The first part or shaft 76, which protrudes from the second part or block 78, is lubricated on its exterior and fits for smooth rotation into a correspondingly shaped aperture 87 that extends through the valve body 72.

A central supply passage 86 comprising a central bore extends through the shaft 76 and part way into the block 78. The face of the shaft has a barbed connector 88 fastened thereto so that flexible-tube air control line 36 may be connected thereto in communication with the passage 86.

The innermost end of the supply passage 86 terminates in a manifold 99 formed inside of the block 78 of the selector (FIG. 5). The manifold 99 distributes the supply air to three branches 92, 94, 96 that extend through the block 78 and open to the planar, outlet surface 82 (FIG. 4A) of the selector block 78. The three manifold outlets 93, 95, 97 at the block surface 82 are respectively located in the six o'clock, four o'clock and two o'clock positions when viewed in FIG. 4A, where the selector handle 32 is in the "0" position.

It will be appreciated that the manifold 99 may be formed by any of a number of ways. In one embodiment, blind holes are drilled into the surface 82 of the selector block, concentric with the outlets 93, 95, 97. Transverse holes 73, 75 are drilled through a flat 77 on the block 78 to join the blind holes that are aligned with two of the outlets 95, 97. A third hole 79 (FIG. 3) is formed to connect the other outlet 93, transverse holes 73, 75 and supply passage 86. This hole 79 is plugged with the end of the selector handle 32, which is bonded thereto. Spherical plugs 81 are fastened to seal the ends of the transverse holes 73, 75.

Surrounding each manifold outlet 93, 95, 97 is a counterbored region into which snugly fits an O-ring 90. Each O-ring 90 protrudes slightly from surface 82 so that the O-ring is compressed slightly to seal the respective manifold outlet as the selector 74 is assembled with the outlet surface 82 immediately adjacent a planar, inner surface 84 on the valve body 72.

The shaft of the selector (FIG. 3) protrudes beyond the outer surface of the valve body 72 and includes a groove 53 formed therein. The groove 53 protrudes just beyond the outer surface 51 of the valve body and receives a retainer clip 55 that is snapped into the groove. The retainer clip 55 extends radially outwardly from the groove by an amount sufficient to prevent the shaft 76 from backing out of the aperture 87 in the valve body.

The valve body 72 includes three through-conduits 100, 102, 104 that extend completely through the valve body from the inner surface 84 to the outer surface 51 of the valve body. At the outer surface 51, the conduits terminate in barbed connectors 101, 103, 105 to which the control lines 54, 38, 40 are respectively connected. The line 54 to the above-described support assembly 50 is connected to the connector 101 of conduit 100. The first handpiece control line 38 is connected to the connector 103 of conduit 102, and the second handpiece control line 40 is connected to the connector 105 of conduit 104.

For ease of illustration, the locations of the valve body conduits are shown in FIGS. 4 and 5 as dashed-line holes with cross markings.

Three exhaust recesses 106, 108, 110 are formed in the selector block outlet surface 82. Those recesses and the facing surface portions of the inner surface 84 of the valve body define exhaust ports to atmosphere, the function of which will be described.

When the selector is in position "0", one of the exhaust ports or recesses 106 is aligned with the conduit 100 that connects with the support assembly control line 54. Accordingly, when the selector is in position "0" any air in line 54 is exhausted to atmosphere and the feet 52 are retracted as explained earlier.

When the selector handle 32 is moved to rotate the selector to position "1" (FIG. 4B), one of the manifold outlets 93 (which was previously located in the six o'clock position) is relocated into a position whereby it is aligned with the valve conduit 104. Consequently, the control air supplied via passage 86 passes into conduit 104 for pressurizing the connected control line 40 for preventing flow of drive air to the second handpiece 28, as explained earlier.

When the selector is in position "1" a second outlet 95 aligns with the valve conduit 100 that is connected to the control line 54 that delivers pressurized air to the support assemblies 50. Consequently, air supplied through passage 86 is directed to the assemblies 50 via line 54 for extending the pistons to raise the base 22 off its wheels 37.

When the selector is in position "1" an exhaust port 108 on the selector block is aligned with conduit 102 so that the control line 38 is exhausted, thereby to permit drive air to pass through the control block 42 to the first handpiece 26, as described above. Accordingly, position "1" can be considered the first handpiece activation position.

When the selector is moved to position "2" (FIG. 4C), one manifold outlet 97 is aligned with the conduit 100 for directing air through line 54 for extending the support pistons 52. In position "2" the manifold outlet 93 is aligned with the valve conduit 102 for pressurizing control line 38, thereby preventing the drive air from flowing to the first handpiece 26. In position "2", the exhaust port 110 is substantially aligned with conduit 104, thereby to exhaust air in control conduit 40, hence permitting flow of drive air through the valve block 42 to operate the second handpiece 28. Position "2", therefore, may be considered the second handpiece activation position.

With reference to FIG. 3, it is noteworthy that the valve body is assembled with a detent mechanism comprising a spring 120 that is retained in a hole 122 to urge a sphere 124 against the outer surface of the shaft 76 of the selector. The shaft surface has formed therein three spaced-apart grooves 130, 132, 134 (FIG. 4B). One of each of the grooves aligns with the sphere 124 when the selector is in position "0", "1" or "2" so that the sphere 124 is forced into the groove to serve as a detent mechanism for holding the selector in the selected position until the detent mechanism is overcome by the manual rotation of the selector by the user. Preferably, the groove 132 associated with the neutral position "0" is deeper than the others, hence requiring a slightly more deliberate manipulation to move the selector out of the neutral position.

Stop pins 33 are attached to the surface 84 of the valve body to extend from surface 84, thereby to prevent the selector from being rotated from position "0" beyond positions "1" or "2".

Although the foregoing has been described in connection with preferred and alternative embodiments, it will be appreciated by one of ordinary skill in the art that various modifications may be substituted for the mechanisms and method described here without departing from the invention as defined by the appended claims and their equivalents.

The invention claimed is:

1. A portable dental pneumatic system comprising:

a first pneumatically driven dental handpiece;

a base member for supporting said first dental handpiece, said base member having rotatable wheels positioned at a bottom surface of the base member;

at least one air driven support assembly mounted at a bottom surface of the base member, said support assembly having a retractable piston which is activated by pressurized air to extend from the base member to lift the base member wheels off the floor; and a pneumatic control system supported by said base member for receiving air from a pressurized source and controlling the operation of said first pneumatically driven dental handpiece and said air driven support assembly, wherein said pneumatic control system includes a manually actuated valve assembly having a neutral position in which neither the first handpiece nor the support assembly is activated and a first position in which the first handpiece and the support assembly are activated.

2. The system of claim 1 further comprising a second pneumatically driven dental handpiece, the second dental handpiece being supported by the base number;

and wherein in the neutral position, the second handpiece is not activated, in the first position, the second handpiece is not activated, and in which the manually actuated valve assembly has a second position, in which the second handpiece and the support assembly are activated and the first handpiece is not activated.

3. The system of claim 2 in which the valve assembly comprises:

a valve body having holes for connection with first, second, and third pneumatic conduits and having a planar surface to which the holes open, the support assembly adapted to be connected to the first conduit, the first handpiece adapted to be connected to the second conduit, and the second handpiece adapted to be connected to the third conduit; and a selector rotatably coupled with the valve body, the selector having a selector body, the selector body including:

a supply passage for receiving pressurized source air;

a manifold connected to the supply passage to receive the source air and having branches for distributing the source air to three outlets of the manifold;

exhaust ports defined therein adjacent the outlets; and a planar, outlet surface that abuts the planar surface of the valve body and slides relative thereto, the three outlets opening to the outlet surface;

the selector being rotatable into the neutral position for connecting one of the first, second, and third conduits to an exhaust port for relieving pressure in the one conduit, and into the first position for connecting two of the three conduits to the manifold to pressurize the two conduits while connecting the third one of the conduits to an exhaust port.

4. The system of claim 3 wherein none of the manifold outlets aligns with a hole when the selector is in the neutral position.

5. The system of claim 3 wherein each of only two of the manifold outlets aligns with a hole when the selector is in the first position.

6. The system of claim 3 wherein in the second position, the selector connects a different two of the three conduits to the manifold than are connected to the manifold in the first position to pressurize the two conduits while connecting the third one of the conduits to an exhaust port.

7. The system of claim 6 wherein each of only two of the manifold outlets aligns with a hole when the selector is in the second position.

8. The system of claim 6 wherein a same one of the holes is aligned with a manifold outlet irrespective of whether the selector is in the first or second position.

9. The system of claim 3 further comprising resilient seal members mounted within recesses in the outlet surface to surround each of the manifold outlets.

10. The system of claim 3 further comprising a control block for connecting to at least one of the conduits, the control block defining a passage and a chamber adjacent the passage, the passage being connectable to a supply of drive air and the chamber being connectable to the one of the conduits, the control block also including a diaphragm adjacent both the passage and chamber, the diaphragm being movable into a release position within the control block for permitting a supply of drive air to flow through the passage, the diaphragm also being movable into a closed position for preventing flow of the drive air through the passage, and wherein pressurizing the one of the conduits moves the diaphragm to the closed position.

11. The system of claim 10 in which the control block further defines a second passage and a second chamber, the second passage being connectable to another of the conduits, the control block also including a second diaphragm that is movable into a release position within the control block for permitting a supply of drive air to flow through the second passage, the second diaphragm also being movable into a closed position for preventing the flow of drive air through the second passage, and wherein pressurizing the another conduit moves the second diaphragm to the closed position.

12. A valve system for selectively pressurizing and exhausting three pneumatic conduits of a dental system comprising:

a valve body having holes for connection with first, second, and third pneumatic conduits; and a selector rotatably mounted to the valve body, the selector having a body, the body including:
a supply passage for receiving pressurized source air;
a manifold connected to the supply passage to receive the source air and having branches for distributing the source air to three outlets of the manifold;
exhaust ports defined therein;

the selector being rotatable into a neutral position for connecting one of the first, second, and third conduits to an exhaust port for relieving pressure in the one conduit, and into a first position for connecting two of the three conduits to the manifold to pressurize the two conduits while connecting the third one of the conduits to an exhaust port; and a control block for connecting to at least one of the conduits, the control block defining a control block passage and a control block chamber adjacent the control block passage, the control block chamber being connectable to one of the conduits, the control block also including a diaphragm adjacent both the control block passage and control block chamber, the diaphragm being movable into a release position within the control block for permitting a supply of drive air from said source to flow through the passage in the block, the diaphragm also being movable into a closed position for preventing flow of the drive air through the passage in the block, whereby pressurizing the one of the conduits moves the diaphragm to the closed position.

13. The system of claim 12 wherein the control block is adapted to be connected to another of the conduits, the control block defining a second passage and second chamber and including a second diaphragm adjacent both the second passage and second chamber, the second diaphragm being movable into a release position within the control block for permitting a supply of drive air from said source to flow through the second passage in the block, the second diaphragm also being moveable into a closed position for preventing flow of the drive air through the second passage in the block, whereby pressurizing the another conduit moves the second diaphragm to the closed position.

* * * * *